United States Patent [19]

Degner et al.

[11] Patent Number: 4,820,389
[45] Date of Patent: Apr. 11, 1989

[54] NOVEL BENZALDEHYDE DIALKYL ACETALS AND PREPARATION AND USE THEREOF

[75] Inventors: Dieter Degner, Dannstadt-Schauernheim; Walter Gramlich, Edingen-Neckarhausen; Franz Lanzendoerfer, Ellerstadt; Hardo Siegel, Speyer, all of Fed. Rep. of Germany

[73] Assignee: BASF Aktiengesellschaft, Ludwigshafen, Fed. Rep. of Germany

[21] Appl. No.: 181,120

[22] Filed: Apr. 13, 1988

[30] Foreign Application Priority Data

Apr. 24, 1987 [DE] Fed. Rep. of Germany ....... 3713732

[51] Int. Cl.$^4$ ............................................... C25G 3/02
[52] U.S. Cl. ...................................... 204/78; 568/592
[58] Field of Search ........................... 468/425; 204/78

[56] References Cited

U.S. PATENT DOCUMENTS

| | | | |
|---|---|---|---|
| 2,450,878 | 10/1948 | Carpenter et al. | 260/599 |
| 2,476,515 | 7/1949 | Stevens | 171/252 |
| 4,318,783 | 3/1982 | Buhmann et al. | 204/79 |
| 4,539,081 | 9/1985 | Degner et al. | 204/78 |

*Primary Examiner*—R. L. Andrews
*Attorney, Agent, or Firm*—John H. Shurtleff

[57] ABSTRACT

Benzaldehyde dialkyl acetals of the formula

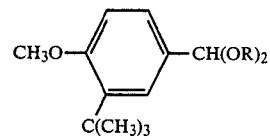

where R is alkyl of 1 to 4 carbon atoms, are prepared by electrochemical oxidation of 3-tert-butyl-4-methoxytoluene in the presence of an alkanol of the formula ROH and are used as scents or scent intermediates.

7 Claims, No Drawings

NOVEL BENZALDEHYDE DIALKYL ACETALS AND PREPARATION AND USE THEREOF

The present invention relates to novel benzaldehyde derivatives and to the preparation and use thereof as scents and scent intermediates.

Acetals of benzaldehydes, being appreciably more stable in alkaline media than the aldehydes, are extensively used in perfumery, in particular in the perfuming of industrial products. Existing commercial products include benzaldehyde dimethyl acetal (sweetly green scent), benzaldehyde diethyl acetal (sweet, mild and green scent), anisaldehyde dimethyl acetal (tangy green, somewhat floral scent) and also anisaldehyde diethyl acetal (floral sweet, slightly green scent).

We have now found that the novel benzaldehyde dialkyl acetals of the general formula

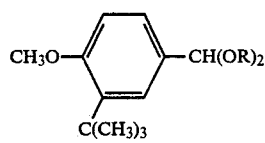 I where R is alkyl of 1 to 4 carbon atoms, are useful scents or scent intermediates. R is for example methyl, ethyl, propyl, isopropyl, butyl or isobutyl.

For instance, the dimethyl acetal of 3-tert-butyl-4-methoxybenzaldehyde has an interesting floral sweet scent with an earthy secondary note, while the corresponding diethyl acetal has an interesting persistant green note.

The novel acetals of the formula I can be prepared in a particularly elegant method of working the invention by oxidizing 3-tert-butyl-4-methoxytoluene of the formula

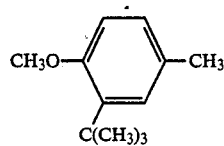 II electrochemically in the presence of an alkanol of the formula ROH where R is alkyl of 1 to 4 carbon atoms.

The alkanol used is preferably methanol or ethanol.

The process according to the invention requires no special cell design, and is preferably carried out in an undivided flow cell. Suitable anodes are for example noble metal electrodes, such as Pt, or oxide electrodes, such as $Ti/RuO_2$. The preferred anode material is graphite. Suitable cathodes are for example steel, iron, nickel, copper, zinc and carbon and also noble metals such as Pt. The preferred cathode material is graphite. The electrolyte is composed of the starting compound of the formula II, the alkanol and a conductive salt. Suitable conductive salts are neutral salts, acids and bases. Examples of neutral salts are fluorides, such as KF, sulfonates, such as $NaSO_3C_6H_5$, sulfates such as $(CH_3)_4NSO_4CH_3$, tetrafluoroborates, such as $NaBF_4$, phosphates and phosphonates. Examples of acids are sulfuric acid, alkylsulfonic acids and arylsulfonic acids. The bases used are for example alkoxides, such as $NaOCH_3$, or hydroxides of the alkali metals, such as KOH.

The electrolyte has for example the following composition:
from 3 to 60% by weight of compound of the formula II
from 35 to 90% by weight of ROH
from 0.5 to 10% by weight of conductive salt.

The current density in the process according to the invention can be varied within wide limits, for example within the range from 0.5 to 20 $A/dm^2$. Preference is given to working at from 1 to 8 $A/dm^2$. The electrolysis temperatures range for example from 20° to 60° C. The electrolysis is preferably carried out under atmospheric pressure. The starting compound II is substantially convertible. Unconverted 3-tert-butyl-4-methoxytoluene can if required be recycled into the electrolysis. The electrolysis can be carried out not only batchwise but also continuously.

The output from the electrolysis is worked up in a conventional manner. If the output gives an acid reaction, it is first neutralized with a base, such as $NaOCH_3$. Excess alkanol is distilled off. The conductive salt is filtered off and can be recycled into the electrolysis together with the alkanol. The crude acetals can be further purified, for example by rectification.

The novel acetals can be converted to 3-tert-butyl-4-methoxybenzaldehyde by hydrolysis with water in a conventional manner. 4-Methoxy-3-tert-butyl-4-methoxybenzaldehyde is a much sought-after scent (empyreumatic scent note of the Russian leather type) which hitherto was prepared from 3-tert-butyl-4-methoxytoluene by manganese oxide oxidation in sulfuric acid solution (U.S. Pat. Nos. 2,450,878, 2,476,515). Since these processes give rise to appreciable amounts of waste salts, the present invention, by providing novel acetals which are easily convertible with water into 3-tert-butyl-4-methoxybenzaldehyde, provides a novel, particularly advantageous way of preparing this scent.

EXAMPLE 1

Electrosynthesis of 3-tert-butyl-4-methoxybenzaldehyde dimethyl acetal

Apparatus: undivided cell containing 11 electrodes
Anodes: graphite
Electrolyte:
  1729 g of 3-tert-butyl-4-methoxytoluene
  60 g of $KSO_3C_6H_5$
  10140 g of $CH_3OH$
Cathodes: graphite
Current density: 3.4 $A/dm^2$
Electrolysis temperature: 26° C.
Electrolysis with 5.2 F/mol of 3-tert-butyl-4-methoxytoluene During the electrolysis the electrolyte is pumped through the cell by way of a heat exchanger at a rate of 200 l/h.

Working up:
On completion of the electrolysis methanol is distilled off under atmospheric pressure at base of column temperatures of up to 120° C. The residue is filtered at from 40° to 50° C. through a suction filter, leaving 75 g of solventmoist salt which can be recycled with the methanol into the electrolysis. The filtrate is subjected to fractional distillation at 6 mbar (top of column pressure) and 80°-125 C., giving 98.7 g of 3-tert-butyl-4-methoxytoluene and 159.4 g of 1-methoxymethyl-3-tert-butyl-4-methoxybenzene, which can both be recycled into the electrolysis, and also 1,408.7 g of 3-tert-butyl-4-methoxybenzaldehyde dimethyl acetal.

HNMR (CDCl$_3$): 1.36 ppm (s) of —C(CH$_3$)$_3$,
5.32 ppm (s) of —CH=,
3.33 ppm (s) of =C(OCH$_3$)$_2$,
6.86 ppm (d) of arom. H,
3.85 ppm (s) of ArOCH$_3$.
7.24–7.33 ppm (s) of arom. H.
n$_D^{20}$: 1.4978.

These figures convert to a conversion, based on 3-tert-butyl-4-methoxytoluene, of 94.3%, a 3-tert-butyl-4-methoxybenzaldehyde dimethyl acetal yield of 60.9% and a 3-tert-butyl-4-methoxybenzaldehyde dimethyl acetal selectivity of 70.5%.

EXAMPLE 2

Electrosynthesis of 3-tert-butyl-4-methoxybenzaldehyde diethyl acetal

Apparatus: undivided cell containing 11 electrodes
Anodes: graphite
Electrolyte:
  450 g of 3-tert-butyl-4-methoxytoluene
  15 g of NaSO$_3$C$_6$H$_5$
  2535 g of C$_2$H$_5$OH
Cathodes: graphite
Current density: 1.7 A/dm$^2$
Electrolysis temperature: 45° C.
Electrolysis with 42 F/mol of 3-tert-butyl-4-methoxytoluene During the electrolysis the electrolyte is pumped through the cell by way of a heat exchanger at a rate of 400 l/h.

Working up:
On completion of the electrolysis, ethanol is distilled off under atmospheric pressure at base of column temperatures of up to 140° C., the residue is filtered at from 30° to 40° C. through a suction filter (residue, solvent-moist: 21 g), and the filtrate is subjected to fractional distillation at 4 mbar (top of column pressure) and 119°–122 C., to give 21.7 g of 3-tert-butyl-4-methoxytoluene and 10.7 g of 1-ethoxymethyl-3-tert-butyl-4-methoxybenzene, which can both be recycled into the electrolysis, and also 491.5 g of 3-tert-butyl-4-methoxybenzaldehyde diethyl acetal (n$_D^{25}$: 1.4883).

HNMR (CDCl$_3$): 1.25 ppm (t) of —CH$_3$, 3.84 ppm (s) of Ar-OCH$_3$,
1.36 ppm (s) of —C(CH$_3$)$_3$, 5.44 ppm (s) of —CH=,
3.47–3.68 ppm (m) of —CH$_2$—,
6.85 ppm (d) of arom. H,
7.25–7.36 ppm (m) of arom. H.

These figures convert to a conversion based on 3-tert-butyl-4-methoxytoluene of 95.2%, a 3-tert-butyl4-methoxybenzaldehydediethyl acetal yield of 73.1% and a 3-tert-butyl-4-methoxybenzaldehyde diethyl acetal selectivity of 78.4%.

EXAMPLE 3

Synthesis of 3-tert-butyl-4-methoxybenzaldehyde 99.4 g of 3-tert-butyl-4-methoxybenzaldehyde dimethyl acetal are refluxed in 300 g of water for 3 hours. This is followed by cooling down, and the residue is filtered off and dried, leaving 77.5 g of 3-tert-butyl-4-methoxybenzaldehyde (mp. 52°–53 C.), which corresponds to a yield of 96.7%.

We claim:

1. A benzaldehyde dialkyl acetal of the formula

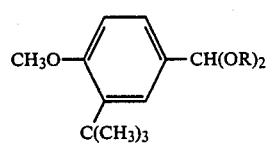

(I)

where R is alkyl of 1 to 4 carbon atoms.

2. 3-tert-Butyl-4-methoxybenzaldehyde dimethyl acetal.

3. 3-tert-Butyl-4-methoxybenzaldehyde diethyl acetal.

4. A process for preparing a benzaldehyde dialkyl acetal as claimed in claim 1, which comprises oxidizing 3-tert-butyl-4-methoxytoluene of the formula

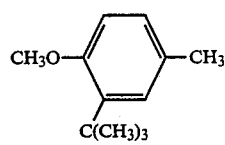

(II)

electrochemically in the presence of an alkanol of the formula ROH where R is alkyl of 1 to 4 carbon atoms.

5. A process as claimed in claim 4, wherein the electrooxidation is carried out in an undivided cell on graphite electrodes.

6. A process as claimed in claim 4, wherein the electrooxidation is performed on an electrolyte containing from 3% to 60% by weight of the compound of the formula II, from 35 to 90% by weight of an alkanol of the formula ROH and from 0.5% to 10% by weight of a conductive salt.

7. A process as claimed in claim 4, wherein the electrooxidation is carried out with a current density of from 0.5 to 20 A/dm$^2$ at from 20° to 60° C.

* * * * *